United States Patent [19]
Renken, Jr.

[11] 3,930,405
[45] Jan. 6, 1976

[54] METHOD AND MEANS FOR MEASURING ACOUSTIC EMISSIONS

[75] Inventor: Claus J. Renken, Jr., Holts Summit, Mo.

[73] Assignee: The United States of America as represented by the United States Energy Research and Development Administration, Washington, D.C.

[22] Filed: Sept. 17, 1974

[21] Appl. No.: 506,819

[52] U.S. Cl............ 73/71.4; 324/60 CD; 324/61 R
[51] Int. Cl.²...................... G01D 7/00; G01N 9/18
[58] Field of Search........ 340/15; 324/60 CD, 61 R; 179/106, 111 E, 111 R; 178/DIG. 10; 320/1; 73/67, 522, 71.4, 88 AE

[56] References Cited
UNITED STATES PATENTS

| | | | |
|---|---|---|---|
| 2,788,516 | 4/1957 | Girerd | 324/60 CD |
| 3,604,251 | 9/1971 | Dixon | 179/111 R |
| 3,716,782 | 2/1973 | Henry | 324/60 CD |
| 3,824,459 | 7/1974 | Uchinda | 324/60 CD |

*Primary Examiner*—Maynard R. Wilbur
*Assistant Examiner*—T. M. Blum
*Attorney, Agent, or Firm*—Dean E. Carlson; Arthur A. Churm; Paul A. Gottlieb

[57] ABSTRACT

The detection of acoustic emissions emanating from an object is achieved with a capacitive transducer coupled to the object. The capacitive transducer is charged and then allowed to discharge with the rate of discharge being monitored. Oscillations in the rate of discharge about the normally exponential discharge curve for the capacitive transducer indicate the presence of acoustic emissions.

2 Claims, 5 Drawing Figures

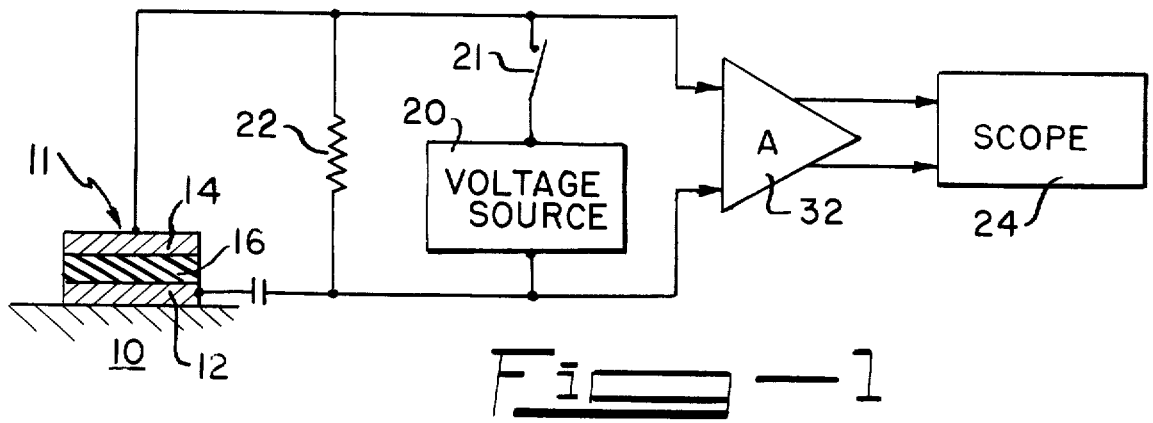
Fig—1
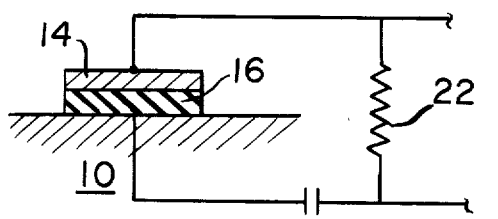
Fig—2
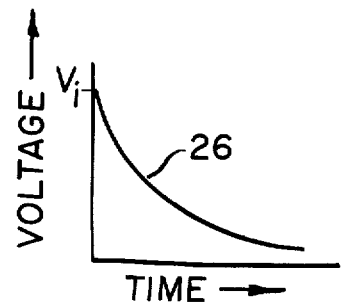
Fig—3
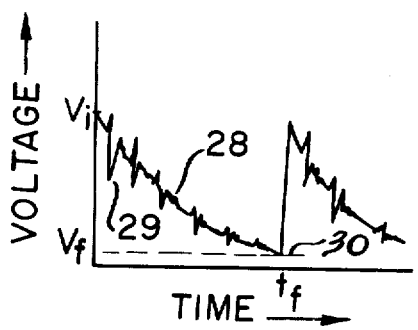
Fig—4
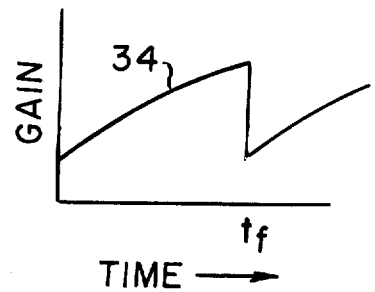
Fig—5

METHOD AND MEANS FOR MEASURING ACOUSTIC EMISSIONS

CONTRACTUAL ORIGIN OF THE INVENTION

The invention described herein was made in the course of, or under, a contract with the United States Atomic Energy Commission.

BACKGROUND OF THE INVENTION

An acoustic emission is a generally nonaudible noise caused by minute changes in a material or object due to stresses imposed thereon. Thus, when a material undergoes a permanent plastic deformation, it will generate a sound which may be monitored by ultrasensitive means.

This phenomenon can be used, for example, to monitor nuclear reactor vessels for material and structural failures such as fuel rod cracks. Since the bulk of acoustic emissions are inaudible, it is necessary to detect them by means of transducers which are placed at various locations on the surface of the object or vessel to be tested. The more sensors which can be present, then the greater the likelihood of detecting and locating a material failure. Therefore, the range of response and the cost of each individual transducer becomes of prime importance. Presently available transducers of sufficient sensitivity, typically piezoelectric crystals, usually only provide a narrow band of frequency response to acoustic emissions and are relatively quite expensive.

It is therefore an object of this invention to provide a transducer device for detecting acoustic emissions from objects.

Another object of this invention is to provide an inexpensive broadband detector of acoustic emissions.

Another object of this invention is to provide a method for detecting acoustic emissions from objects.

SUMMARY OF THE INVENTION

A method and means are provided for monitoring the acoustic emissions of an object such as a nuclear reactor vessel. A capacitive transducer is coupled to the object and then charged to an initial voltage. The capacitive transducer is then allowed to discharge across a load with the voltage across the load, which corresponds to the charge on the capacitor at that instant, being observed by monitoring means. The rate of this discharge is normally a smooth exponential discharge curve. Oscillations about the normally exponential discharge curve, as observed by the monitoring means, indicate the occurrence of acoustic emissions in the object during the discharging of the transducer. Decrease in the amplitude of the oscillations as the amplitude of the capacitive transducer's charge decreases is compensated for by amplifying the voltage signal across the load with an automatic gain control amplifier and then observing with the monitoring means the amplified signal. When the charge on the capacitive transducer has decreased to about 20 percent of the initial charge, the amplitude of the oscillations associated with the acoustic emissions becomes too small with respect to noise to be of value and the capacitive transducer should be recharged for continuous operation.

BRIEF DESCRIPTION OF THE DRAWINGS

FIG. 1 is a schematic of a device for detecting acoustic emissions;

FIG. 2 is an alternate embodiment of the device of FIG. 1;

FIG. 3 is a curve showing the normally exponential discharge curve of a capacitive transducer;

FIG. 4 is a curve showing the discharge curve of a capacitive transducer with acoustic emissions present; and FIG. 5 is a curve showing the output of the AGC amplifier.

DETAILED DESCRIPTION OF THE PREFERRED EMBODIMENT

Referring to FIGS. 1 and 2, there is shown a device for detecting acoustic emissions from an object 10 which may be any type of object to which a capacitive transducer may be coupled, such as a nuclear reactor vessel. Generally, for the purposes of this invention, a capacitive transducer is a capacitive device which may be charged to an initial voltage and then when allowed to discharge will discharge at a rate which depends, among other things, upon physical forces applied to it. Discharging of a capacitive device is the reduction of the potential difference between the electrodes of the device toward zero value and normally follows an exponential curve. The rate of discharge of the discharge curve is the speed at which this reduction occurs and may be illustrated graphically by a curve showing the potential difference with respect to time.

The capacitive transducer 11 includes a first electrode 12, a second electrode 14, and a dielectric material 16 disposed between electrodes 12 and 14. Electrode 12 is mounted in physical contact with object 10 by any of several well-known means for providing a coupling between a transducer and an object. FIG. 2 shows an alternate embodiment for capacitive transducer 11. If the object 10 is of metal, it may be used as the electrode 12 as shown in FIG. 2 and the dielectric is then disposed between the object 10 and the other electrode 14. Any vibrations of object 10, particularly those associated with acoustic emissions, will therefore be transferred from the object to transducer 11, in effect varying the spacing between the electrodes according to the vibrations.

With switch 21 closed, a voltage source 20 applies a voltage across electrodes 12 and 14, charging the capacitive transducer 11 to an initial value $V_i$. When $V_i$ has been reached switch 21 is opened, and a simple parallel RC circuit is created with capacitive transducer 11 and resistor 22. The voltage across resistor 22, which corresponds to the potential difference between the electrodes of capacitive transducer 11, as is well known, will decrease. This is because capacitive transducer 11 will begin to discharge when switch 21 is opened. Without interference, this discharge of capacitive transducer 11 and the corresponding reduction in voltage across resistor 22 will normally be exponential. Thus, the discharge curve will be smooth and normally exponential as shown by curve 26 of FIG. 3. The decrease in voltage across resistor 22, the discharge curve, is monitored by suitable monitoring means such as an oscilloscope 24, which produces a display of the decrease in voltage across resistor 22 as capacitive transducer 11 discharges, the discharge curve 26 of FIG. 3 with $V_i$, the initial charge, being the peak value of the normally exponential discharge curve 26.

It has been discovered, however, that with acoustic emissions present during the discharge of the capacitive transducer 11, the rate of discharge will be modulated about the normally exponential rate of discharge as shown by curve 28 of FIG. 4, due to the varied spacing between the electrodes associated with the variations of object 10. The modulations in the discharge curve 28, such as that occurring at point 29, are caused by acoustic emissions from object 10. In particular, detector 11 is responsive to a very wide band of frequencies of acoustic emissions, and the response of the detector 11 to acoustic emissions is characterized by a fast rise time. These are qualities not usually found in an acoustic emission detector.

As the discharging continues, the amplitude of the modulations decreases until, at point $t_r$, where the voltage across resistor 22 is $V_r$, the modulations become too small with respect to noise to be of use. It has been observed that the voltage at the point, $t_f$, i.e. $V_r$, where the modulations are too small, is generally about 0.2 of the initial voltage $V_i$. Therefore, for continuous monitoring of acoustic emission, the capacitive transducer should be recharged or pulsed at time intervals of $t_r$. This can be done by operation of switch 21 or by using a pulsed voltage source. To offset the reducing amplitude of the modulations as the discharging continues, the voltage across resistor 22 may be applied to an amplifier 32, such as an automatic gain control (AGC), before monitoring by scope 24. The AGC amplifier 32 has a gain associated with the discharge curve applied to it as shown by curve 34 of FIG. 4. The value of the gain of an AGC varies inversely to the value of the signal it is amplifying. Therefore the output of amplifier 32 will be a more uniform signal in that the lower values of the discharge curve will receive more amplification than the higher values. Best results can be obtained with the time constant of the AGC short with respect to the time constant of the discharge curve and long with respect to the modulations so that the modulations are not smeared by the amplification. However, because of the modulation signal-to-noise ratio at the lower values, for continuous operation, pulsing is still required.

The maximum value of $V_i$, the initial charge on capacitive transducer 11, is limited by the breakdown voltage of the dielectric 16 while the minimum value of $V_i$ is limited by the amount of noise present in the circuit which will smother the acoustic modulations. The amount of noise will depend, among other things, upon the type of dielectric and its thickness. Generally, any type of dielectric 16 will produce the modulation effect described; however, the least noise with respect to the modulations is achieved with a dielectric 16 having a high E field impressed upon it by a relatively low voltage between electrodes 12 and 14. Since an E field strength for a capacitor is defined as the voltage between the plates divided by the distance between the plates, best results are obtained if dielectric 16 is a thin dielectric such as mica. The minimum E field which will give a usable rate of discharge to at least 0.2 of $V_i$ before noise smothers the modulations is about 0.5 volts/mil, with best results being between 2 and 5 volts/mil. For example, for a mica dielectric, best results were obtained with a thickness of 2 to 5 mils with a voltage between electrodes 12 and 14 of about 10 volts. Of course, other well-known thin dielectrics are applicable, as would be apparent to those skilled in the art.

In practice, numerous acoustic sensors are positioned about the object in order to pinpoint the location of the source of the acoustic emission within the object, such as by methods similar to triangulation. For example, in a nuclear reactor numerous capacitive transducers may be placed about the containment vessel. When an acoustic emission test is desired, such as when a fuel rod failure is suspected, each transducer may be simultaneously charged and then allowed to discharge. The rate of discharge may be monitored for modulations indicating acoustic emissions and for the time of arrival of the acoustic emission at each transducer. By comparing the time of arrival at each transducer and by applying well-known calculation methods, the source of the emissions may be located. Because of the inexpensive nature of the transducer herein required and because of the wide band frequency response of the transducer, the accuracy and expense of such an acoustic emission system is reduced.

The embodiments of the invention in which an exclusive property or privilege is claimed are defined as follows:

1. A device for monitoring acoustic emissions from an object, comprising:

a capacitive transducer having two electrodes and a thin dielectric of mica between 2 and 5 mils thick disposed therebetween, one of said electrodes being mechanically coupled to the object, a pulsed voltage source coupled to and capable of charging said capacitive transducer to an initial voltage $V_i$ between said electrodes such that the E field impressed upon said dielectric is at least 0.5 volt/mil, a load coupled across said capacitive transducer for discharging said capacitive transducer to a voltage less than $V_i$, said source being responsive to the voltage between said electrodes being 0.2 $V_i$ to recharge said capacitive transducer to $V_i$, with said capacitive transducer discharging across said load the rate of change in the voltage across said load being proportional to the normally exponential rate of discharge of said capacitive transducer, an AGC amplifier coupled to said load, and being responsive to the voltage across said load to develop an output signal being the amplification of the voltage across said load with a magnitude of amplification inversely proportional to the value of the voltage across said load, and monitoring means coupled to said AGC amplifier and responsive to the output voltage thereof to detect modulations in said output signal from that which said output signal would be due to said normally exponential rate of change of the voltage across said load, the time constant of said AGC amplifier being shorter than the time constant of said normally exponential rate of discharge and longer than the time constant of said modulations, said modulations indicating the presence of acoustic emissions from the object.

2. The device of claim 1 wherein the E field impressed upon said dielectric is between 2 and 5 volt/mil.

* * * * *